US009841390B2

(12) United States Patent
Radley et al.

(10) Patent No.: US 9,841,390 B2
(45) Date of Patent: Dec. 12, 2017

(54) IDENTIFICATION OF MATERIALS FROM A HYDROGEN TO ELECTRON RATIO

(71) Applicant: Kromek Limited, Sedgefield (GB)

(72) Inventors: Ian Radley, Sedgefield (GB); Benjamin John Cantwell, Sedgefield (GB); Andrew Keith Powell, Sedgefield (GB)

(73) Assignee: Kromek Limited, Sedgefield (GB)

( * ) Notice: Subject to any disclaimer, the term of this patent is extended or adjusted under 35 U.S.C. 154(b) by 0 days.

(21) Appl. No.: 14/441,999

(22) PCT Filed: Nov. 11, 2013

(86) PCT No.: PCT/GB2013/052956
§ 371 (c)(1),
(2) Date: May 11, 2015

(87) PCT Pub. No.: WO2014/076462
PCT Pub. Date: May 22, 2014

(65) Prior Publication Data
US 2015/0300967 A1    Oct. 22, 2015

(30) Foreign Application Priority Data
Nov. 13, 2012  (GB) .................................. 1220419.4

(51) Int. Cl.
*G01N 24/08*    (2006.01)
*G01R 33/16*    (2006.01)
*G01N 23/083*    (2006.01)
*G01R 33/46*    (2006.01)

(52) U.S. Cl.
CPC ........... *G01N 24/08* (2013.01); *G01N 23/083* (2013.01); *G01R 33/16* (2013.01); *G01R 33/46* (2013.01)

(58) Field of Classification Search
CPC ........ G01N 23/02; G01N 23/08; G01N 23/10; G01N 23/083; G01R 33/44; G01R 33/4812; A61B 6/032; A61B 6/482; A61B 6/583; A61B 6/585
See application file for complete search history.

(56) References Cited

U.S. PATENT DOCUMENTS

| 4,149,081 A | 4/1979 | Seppi |
| 4,571,491 A | 2/1986 | Vinegar et al. |
| 5,930,326 A | 7/1999 | Rothschild et al. |
| 7,697,657 B2 | 4/2010 | Walter et al. |
| 8,781,072 B2 * | 7/2014 | Robinson ............. G01N 23/087 378/88 |
| 2001/0004395 A1 * | 6/2001 | McCrory ........... A61K 49/0409 378/162 |
| 2009/0129544 A1 | 5/2009 | Chen et al. |
| 2013/0285657 A1 * | 10/2013 | Espy ..................... G01R 33/44 324/309 |

FOREIGN PATENT DOCUMENTS

| GB | 2285506 A | 7/1995 |
| JP | S53134387 A | 11/1978 |
| JP | H10318951 A | 12/1998 |
| JP | 2004108994 A | 4/2004 |
| JP | 2007082663 A | 4/2007 |
| JP | 20098441 A | 1/2009 |
| JP | 200942134 A | 2/2009 |
| JP | 200953090 A | 3/2009 |
| JP | 2009515190 A | 4/2009 |
| JP | 2009122043 A | 6/2009 |
| JP | 2009122108 A | 6/2009 |
| WO | WO-9802763 A1 | 1/1998 |
| WO | WO2007056420 A2 | 5/2007 |
| WO | WO-2011094686 A2 | 8/2011 |
| WO | WO-2014076461 A1 | 5/2014 |

OTHER PUBLICATIONS

Raguin, Guy, "International Search Report," prepared for PCT/GB2013/052956, dated Jul. 14, 2014, four pages.
Anderson, A.C., et al., "Self-Diffusion Coefficient and Nuclear Susceptibility of Liquid He3," Physical Review Letters, vol. 5, No. 4, Aug. 15, 1960, pp. 133-135.
De Deene, Yves, et al.; "Three Dimensional Radiation in Lung-Equivalent Regions by use of a Radiation Sensitive Gel Foam: Proof of Principle"; Medical Physics, vol. 33, No. 7; Jun. 26, 2006; pp. 2586-2597.

* cited by examiner

*Primary Examiner* — David E Smith
*Assistant Examiner* — Hsien Tsai
(74) *Attorney, Agent, or Firm* — Winstead PC

(57) ABSTRACT

A method of examination of an object comprising the steps of: applying a Nuclear Magnetic Resonance technique to obtain a data item correlated to the relative nuclear susceptibility within the sample; obtaining a further data item correlated to another measure of the object under examination; determining therefrom a ratio.

8 Claims, No Drawings

IDENTIFICATION OF MATERIALS FROM A HYDROGEN TO ELECTRON RATIO

The invention relates to a method for the identification of materials using high energy radiation such as X-rays or gamma-rays and Nuclear Magnetic Resonance. The invention makes use of a ratio technique using NMR and for example a Hydrogen to Electron Ratio technique.

The invention particularly relates to an apparatus and method making use of high energy radiation such as x-rays or gamma-rays to scan objects where it is desirable to gain information about the internal contents and/or composition of the contained material.

Many traditional materials identification techniques use the density of a liquid for accurate identification. These include X-ray and Nuclear Magnetic Resonance techniques.

NMR makes measures of the T1 and T2 relaxation times, which can be used to identify to some success. The Relative Nuclear Susceptibilty is a measure of the total measure of susceptibility derived, for example, from all of the Hydrogen nuclei in the object under examination. Because this is a measure related to the total volume, normally this has to be converted into a susceptibility per unit volume to turn this into a materials characteristic, of the same type as T1 and T2.

In accordance with the invention a method of examination of an object for the identification and detection of the composition the object comprises the steps of:
 applying a Nuclear Magnetic Resonance technique to obtain a data item correlated to the relative nuclear susceptibility within the sample;
 obtaining another data item correlated to another measure of the object under examination, in particular the total number of electrons;
 determining therefrom a ratio.

Conveniently in a further step the method comprises using the ratio to derive an indication of the material content of the sample.

The key to the invention lies in the use of a Nuclear Magnetic Resonance technique to obtain a data item correlated to the relative nuclear susceptibility within the sample which can be co-processed with the another data item correlated to another measure of the object under examination, in particular the total number of electrons, to derive a ratio from which it is possible to draw inferences about the material content without requiring measurement of the volume.

By this method, we avoid ever requiring to know the volume of the object under consideration.

In a preferred embodiment, a method of examination of an object for the identification and detection of the composition the object comprises the steps of:
 irradiating an object under test with high energy radiation such as x-rays or gamma-rays and collecting radiation emergent from the object at a suitable detector system in such manner that emergent radiation intensity data is collected for the entire volume of the object under test;
 numerically processing the radiation intensity data to obtain a first data item correlated to the total number of electrons within the sample;
 applying a Nuclear Magnetic Resonance technique to obtain a second data item correlated to the total number of hydrogen atoms within the sample;
 determining therefrom a Hydrogen to Electron Ratio (HER).

Conveniently in a further step the method comprises using the HER to derive an indication of the material content of the sample.

This invention removes the requirement to measure the volume by using an x-ray measurement together with Nuclear Magnetic Resonance, to obtain a Hydrogen to Electron Ratio (HER).

The key to the preferred embodiment lies in the use of the radiological technique to obtain a data item correlated to the total number of electrons within the object in conjunction with a Nuclear Magnetic Resonance technique to obtain a second data item correlated to the total number of hydrogen atoms within the sample which can be co-processed with the first to determine the HER from which it is possible to draw inferences about the material content without requiring measurement of the volume. Both data items are derived as total numbers integrated over the volume under investigation, so that knowledge of the volume of the sample is no longer required.

The radiation preferably comprises high-energy radiation such as ionising radiation, for example high-energy electromagnetic radiation such as x-rays and/or gamma rays, and the detection system is adapted correspondingly to detect radiation in this spectrum. The radiation is for example from a broadband source such as a broadband x-ray or gamma-ray source capable of producing broad spectrum emission over a wide range of energies.

In accordance with the method of the invention the radiological technique is used to derive a first data item correlated to the total number of electrons within the sample. This may be done in particular by collecting transmitted intensity information and deriving a measurement of the attenuation by the object to derive a measure of the total number of electrons within a sample.

When an X-ray passes through a medium, there are two main methods in which it can be attenuated:
 At low energy, the Photoelectric effect dominates, in which the photon's energy is transferred to an electron orbiting the atom.
 At higher energies, Compton Scattering takes place, where the photon is scattered off the electrons around the atoms.

Both processes are dependent upon the number of electrons in the path of the X-ray, although not in the same proportion. For example, at low energies for material with an atomic number great than about 10 electron shell effects play a role. Thus the dependence of the absorption on the number of electrons in the beam is also energy dependent.

This invention relates to utilising this phenomenon to obtain a measure of the total number of electrons within a sample (using this X-ray Shadow Technique), and subsequently using this information with an orthogonal technique to collect material identification information.

One embodiment of the X-ray Shadow Technique is to irradiate an entire object with a wide beam of X-rays, and collect the intensity information on an array of detectors. Different embodiments to gather information on an entire sample range from one single large-size detector, using a movable single detector to scan the entire item, a linear array of a number of pixels with the sample on a belt, through to a two-dimensional arrays of detectors capturing the entire sample at the same time.

With X-ray information collated over the entire volume through whatever embodiment, the electron count may be calculated from the absorption integrated over all detectors.

As a first approximation, the linear attenuation coefficient ($\mu$) of a material at a given energy $$\mu \propto \rho_e$$

And setting $\beta$ at the constant of proportionality to the electron density $\rho_e$ then $$\mu = \beta \rho_e$$

For the Beer Lambert equation for the output intensity I of a beam at a given energy emerging from a medium of thickness t having incident intensity $I_o$, the transmission T is given by $$T = \frac{I}{I_o} = e^{-\mu t}$$

Taking the logs of both sides, and substituting the earlier equation for the linear attenuation coefficient $$\ln T = -\beta \rho_e t$$

As the X-rays are collected over an area A, we can integrate up over that area $$-\int \beta \rho_e \, t \, dA = \int \ln T \, dA$$

But $$\int t \, dA = V$$

And $$\rho_e = \frac{N_e}{V}$$

Where V is the volume of the sample under investigation and $N_e$ is the number of electrons within that sample.

$$\therefore N_e = \frac{-1}{\beta} \int \ln T \, dA$$

Hence, if a system is calibrated to obtain $\beta$, the number of electrons within the sample can be calculated via a series of transmission measurements.

The embodiment of this invention involves combining this X-ray Shadow Technique with a Nuclear Magnetic Resonance measurement technique, which measures the number of Hydrogen atoms within a sample.

Liquid explosive detection using NMR has been demonstrated using solely the relaxation parameters T1 and T2. These are the parameters which give medical MRI their contrast, and have shown to be highly effective for many materials. These parameters effectively give the number of Hydrogen atoms within the sample under investigation. However, there are some materials which these two parameters alone struggle to classify.

Another parameter which aids material discrimination is the relative nuclear susceptibility, RNS. However, in order to use this method the material volume must be known. The NMR system alone can not give this information, and while other techniques are available which would, such as X-ray CT, they tend to be both expensive and slow. Even these systems are unable to accurately determine the volume of complex irregular objects as presented to a security scanner.

This invention combines the hydrogen content obtained from NMR, and the electron content obtained from X-ray, to give a combined Hydrogen to Electron Ratio (HER) which can be used to identify materials. As both techniques measure total numbers integrated over the volume under investigation, knowledge of the volume of the sample is no longer required.

The invention claimed is:

1. A method of examination of a sample, the method comprising the steps of:
    applying a Nuclear Magnetic Resonance technique to obtain a data item correlated to the relative nuclear susceptibility within the sample;
    obtaining a further data item correlated to another measure of the sample under examination, wherein the further data item correlated to another measure of the sample under examination is the total number of electrons and is obtained by performing a calculation derived from radiation absorption integrated over a whole detection area which calculation includes the following steps:
    performing a series of transmission measurements to determine a radiation transmission, T according to the relationship $$T = \frac{I}{I_o}$$

where I is output intensity of a beam of incident intensity $I_0$ emerging from a medium
    integrating over a whole detection area A according to the relationship $$N_e \beta = -\int \ln T \, dA$$

thereby determining a product correlated to the total number of electrons within the sample, where $\beta$ has been set as a constant of proportionality; and
    determining therefrom a ratio.

2. The method in accordance with claim 1, comprising in a further step the use of the ratio to derive an indication of the material content of the sample.

3. A method of examination of a sample, the method comprising the steps of:
    irradiating the sample under test with high energy radiation such as x-rays or gamma-rays and collecting radiation emergent from the sample at a suitable detector system in such manner that emergent radiation intensity data is collected for the entire volume of the sample under test;
    numerically processing the radiation intensity data to obtain a first data item correlated to the total number of electrons within the sample;
    applying a Nuclear Magnetic Resonance technique to obtain a second data item correlated to the total number of hydrogen atoms within the sample by performing a calculation derived from the radiation absorption integrated over a whole detection area which calculation includes the following steps:
    performing a series of transmission measurements to determine a radiation transmission, T according to the relationship $$T = \frac{I}{I_o}$$

where I is output intensity of a beam of incident intensity $I_0$ emerging from a medium integrating over a whole detection area A according to the relationship $$N_e\beta = -\int \ln T \, dA$$

thereby determining a product correlated to the total number of electrons within the sample, where β has been set as a constant of proportionality; and determining therefrom a Hydrogen to Electron Ratio (HER).

4. The method in accordance with claim 3, comprising in a further step the use of the HER to derive an indication of the material content of the sample.

5. The method in accordance with claim 3, wherein the radiation comprises high-energy ionising radiation.

6. The method in accordance with claim 5, wherein the radiation is derived from a broadband x-ray or gamma-ray source.

7. The method in accordance with claim 1, wherein the further data item correlated to the total number is obtained by performing a calculation derived from the radiation absorption integrated over a whole detection area which calculation includes the following steps:

performing a series of transmission measurements to determine a radiation transmission, T according to the relationship $$T = \frac{I}{I_o} = e^{-\mu t}$$

where I is output intensity of a beam of incident intensity $I_0$ at a given energy emerging from a medium of thickness t and linear attenuation coefficient μ;

integrating over a whole detection area A according to the relationship $$-\int \beta \rho_e t \, dA = \int \ln T \, dA$$

where β has been set as the constant of proportionality to the electron density $\rho_e$;

determining therefrom a total number of electrons within the sample, $N_e$, according to the relationship $$N_e = \frac{-1}{\beta} \int \ln T \, dA.$$

8. The method in accordance with claim 3 wherein the step of numerically processing the radiation intensity data to obtain a first data item correlated to the total number of electrons within the sample comprises performing a calculation derived from the radiation absorption integrated over a whole detection area which calculation includes the following steps:

performing a series of transmission measurements to determine a radiation transmission, T according to the relationship $$T = \frac{I}{I_o} = e^{-\mu t}$$

where I is output intensity of a beam of incident intensity $I_0$ at a given energy emerging from a medium of thickness t and linear attenuation coefficient μ;

integrating over a whole detection area A according to the relationship $$-\int \beta \rho_e t \, dA = \int \ln T \, dA$$

where β has been set as the constant of proportionality to the electron density $\rho_e$;

determining therefrom a total number of electrons within the sample, $N_e$, according to the relationship $$N_e = \frac{-1}{\beta} \int \ln T \, dA.$$

\* \* \* \* \*